United States Patent
Strul et al.

(12)

(10) Patent No.: US 6,293,941 B1
(45) Date of Patent: *Sep. 25, 2001

(54) METHOD AND APPARATUS FOR IMPEDANCE MEASUREMENT IN A MULTI-CHANNEL ELECTRO-SURGICAL GENERATOR

(75) Inventors: Bruno Strul, Portola Valley; Franklin R. Koenig, Palo Alto, both of CA (US)

(73) Assignee: Somnus Medical Technologies, Inc., Sunnyvale, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 09/167,215

(22) Filed: Oct. 6, 1998

Related U.S. Application Data

(60) Provisional application No. 60/061,714, filed on Oct. 6, 1997, provisional application No. 60/061,213, filed on Oct. 6, 1997, provisional application No. 60/062,458, filed on Oct. 6, 1997, provisional application No. 60/061,193, filed on Oct. 6, 1997, provisional application No. 60/061,197, filed on Oct. 6, 1997, and provisional application No. 60/062,543, filed on Oct. 6, 1997.

(51) Int. Cl.[7] ................................................. A01B 18/04
(52) U.S. Cl. .............................. 606/34; 606/41; 606/46; 606/38; 607/101
(58) Field of Search ............................ 606/32, 34, 35, 606/38, 41–50; 607/96–101, 122, 156

(56) References Cited

U.S. PATENT DOCUMENTS

| | | | |
|---|---|---|---|
| 5,233,515 | 8/1993 | Cosman | 364/413.02 |
| 5,496,312 | * 3/1996 | Klicek | 606/34 |
| 5,562,720 | * 10/1996 | Stern et al. | 607/98 |
| 5,697,909 | * 12/1997 | Eggers et al. | 604/114 |
| 5,702,386 | * 12/1997 | Stern et al. | 606/34 |
| 5,810,802 | * 9/1998 | Panescu et al. | 606/31 |

FOREIGN PATENT DOCUMENTS

WO 97/20510   6/1997 (WO) .............................. A61B/17/39

* cited by examiner

*Primary Examiner*—Michael Peffley
*Assistant Examiner*—David Ruddy
(74) *Attorney, Agent, or Firm*—Wilson Sonsini Goodrich & Rosati

(57) ABSTRACT

This invention is an improved method and apparatus for tissue electrical impedance determination and electrical power control in a surgical device.

In an embodiment of the invention an apparatus for controlling power delivery in an electro-surgical instrument is disclosed. The electro-surgical instrument includes a first channel and a second channel for delivery of energy to a surgical site. The apparatus includes: a switch, a measuring unit, a processor and a drive unit. The switch electrically isolates the second channel during a first measurement interval and the first channel during a second measurement interval. The measuring unit is coupled to the first and the second channel. The measurement unit measures a first power level of the first channel during a first measurement interval and a second power level of the second channel during a second measurement interval. The processor is coupled to the measuring unit and to the switch. The processor adjusts the first power level and the second power level to minimize a difference between a measured value of a control parameter and a target value of the control parameter. The drive unit is controlled by the processor. The drive unit delivers the adjusted first and second power levels to the surgical site via respectively the first channel and the second channel during a heating interval.

In an alternate embodiment of the invention a method for controlling power delivery in an electro-surgical instrument is disclosed.

17 Claims, 8 Drawing Sheets

METHOD AND APPARATUS FOR IMPEDANCE MEASUREMENT IN A MULTI-CHANNEL ELECTRO-SURGICAL GENERATOR

CROSS REFERENCE TO RELATED APPLICATION

This application claims the benefit of prior filed copending Provisional Application No. 60/061,213, filed on Oct. 6, 1997, entitled *Method And Apparatus For Impedance Measurement In A Multi-Channel Electro-Surgical Generator*, Provisional Application No. 60/062,458, filed on Oct. 6, 1997, , entitled *Linear Power Control With Digital Phase Lock,* Provisional Application No. 60/061,193, filed on Oct. 6, 1997, , entitled *Linear Power Control With PSK Regulation,* Provisional Application No. 60/061,197, filed on Oct. 6, 1997, entitled *Memory for Regulating Device Utilization and Behavior,* Provisional Application No. 60/061,714, filed on Oct. 6, 1997, entitled *Dual Processor Architecture For Electro Generator,* and Provisional Application No. 60/062,543, filed on Oct. 6, 1997, entitled *Method And Apparatus For Power Measurement In Radio Frequency Electro-Surgical Generators.*

The present application is related to copending U.S. patent application No. 09/167,717, filed Oct. 6, 1998, entitled *Linear Power Control With Digital Phase Lock,* U.S. patent application No. 09/167,412, filed Oct. 6, 1998, entitled *Linear Power Control With PSK Regulation,* U.S. patent application No. 09/167,508, filed Oct. 6, 1998, entitled *Memory for Regulating Device Utilization and Behavior,* U.S. patent application No. 09/167,508, filed Oct. 6, 1998, entitled *Dual Processor Architecture For Electro Generator,* U.S. patent application No. 09/167,505, filed Oct. 6, 1998, entitled *Method And Apparatus For Power Measurement In Radio Frequency Electro-Surgical Generators,* International Application No. PCT/US98/21065 filed Oct. 6, 1998, entitled *Linear Power Control With Digital Phase Lock,* and International Application No. PCT/US98/21066, filed October 1998, entitled *Dual Processor Architecture For Electro Generator.*

Each of the above-cited applications is incorporated herein by reference in its entirety.

BACKGROUND OF THE INVENTION

Field of the Invention

This invention relates to the field of electro-surgical medical devices. More particularly, this invention relates to devices that deliver energy in the form of radio-frequency electrical current to tissue in order to perform surgical functions.

Description of Related Art

Various medical procedures rely on high-frequency electrical currents to deposit energy and thus heat human and animal tissues. During such procedures, a high-frequency current is passed through the tissue between electrodes. One electrode is located at the tip of a surgical probe. Another electrode is located elsewhere, and may be a ground pad or another surgical probe tip. The tissue to be treated lies between the electrodes.

When the electrode circuit is energized, the electric potential of the electrodes at the probe tips oscillates at radio frequencies about a reference potential. If one is used, a ground pad remains at a floating reference potential. As the electric potential of the probe electrodes varies, a motive force on charged particles in the tissue is established that is proportional to the gradient of the electric potential. This electromotive force causes a net flow of electric charge, a current, to flow from one electrode, through the tissue, to any other electrode(s) at a lower potential. In the course of their flow, the charged particles collide with tissue molecules and atoms. This process acts to convert electrical energy to sensible heat in the tissue and is termed Joule heating.

Upon heating, surgical functions such as cutting, cauterizing and tissue destruction can be accomplished. For example, tissues can be cut by heating and eventually vaporizing the tissue cell fluids. The vaporization causes the cell walls to rupture and the tissue to cleave. When it is beneficial to destroy tissue, comparatively higher rates of energy deposition can cause tissue ablation.

Ablation of cellular tissues in situ is used in the treatment of many diseases and medical conditions either alone or combined with surgical removal procedures. Surgical ablation is often less traumatic than surgical removal procedures and may be the only alternative where other procedures are unsafe.

Tissue ablation devices commonly utilize electromagnetic (microwave, radio frequency (RF), lasers) or mechanical (acoustic) energy. In the category of electro-surgical devices, microwave ablation systems utilize a microwave antenna which is inserted into a natural body opening through a duct to the zone of treatment. Electromagnetic energy then radiates from the antenna through the duct wall into the target tissue. However, there is often severe trauma to the duct wall in this procedure since there is a significant microwave energy flux in the vicinity of the intended target. The energy deposition is not sufficiently localized. To reduce this trauma, many microwave ablation devices use a cooling system. However, such a cooling system complicates the device and makes it bulky. Laser ablation devices also suffer the same drawback as microwave systems. The energy flux near the target site, while insufficient to ablate the tissue, is sufficient to cause trauma.

Application of RF electric currents emanating from electrode tips offers the advantage of greater localization of the energy deposition since the electrode tip is nearly a point source. However, these devices require consideration and monitoring of the effect of the energy deposition on the tissue since the electrical dissipation and storage characteristics of the tissue carrying the current may vary with time as a result of the current-induced heating. As a result, the tissue heating response could vary over the time of treatment due to changing values of the tissue's electrical properties.

In addition, the localization of energy flux in an RF electro-surgical device may require a number of electrodes to be included in the surgical probe to provide adequate area coverage. In the case of multiple probe electrodes, each electrode may not be at the same electric potential at each instant due to amplitude, frequency, or phase variations in their RF oscillations. In this instance, an electric current would flow between the probe electrodes, coupling them to an extent primarily determined by the difference in electric potential between the probe electrodes and the electrical properties of the tissue between the electrode tips. This coupling can confuse monitoring of applied power and tissue response.

With an electro-surgical device, the tissue heating response depends largely on the electrical impedance since impedance is a representation of energy dissipation and storage properties. As described, the impedance of the tissue lying between the electrodes is an important parameter in both in the case of a single electrode, as well as in the case of devices with multiple electrodes. In fact, tissue electrical impedance is often displayed to the medical practitioner during a procedure since large changes in tissue impedance are indicative of tissue drying, ablation, etc.. Thus, the efficacy of these devices is critically affected by the methods of tissue electrical impedance determination and power control.

Prior art methods for determining the electrical impedance of the tissue in the context of a device for electro-surgery are of questionable accuracy since the measurements are made at a comparatively low electric current. In the prior art methods, the electric current utilized to determine the impedance is insufficient to damage the tissue. However, the resulting measurements are prone to error since the electrical signals are not strong relative to the noise in the measurement circuit. Prior art methods also do not adequately eliminate electric coupling between the electrodes, termed crosstalk, in the case of a multiple electrode probe. Therefore, there is a need in the field of electro-surgical devices for improved methods and apparatae for tissue electrical impedance determination and electrical power control.

SUMMARY OF THE INVENTION

This invention is an improved method and apparatus for tissue electrical impedance determination and electrical power control in a surgical device. The tissue electrical impedance determination and associated power control is improved relative to the prior art methods in that the uncertainties in determining the actual tissue impedance are reduced in two ways. First, this invention makes the impedance determining measurements less prone to noise-related uncertainties. Second, this invention eliminates measurement uncertainties due to electrical cross-talk between multiple electrode channels.

In an embodiment of the invention, an apparatus for controlling power delivery in an electro-surgical instrument is disclosed. The electro-surgical instrument includes a first channel and a second channel for delivery of energy to a surgical site. The apparatus includes: a switch, a measuring unit, a processor and a drive unit. The switch electrically isolates the second channel during a first measurement interval and the first channel during a second measurement interval. The measuring unit is coupled to the first and the second channel. The measurement unit measures a first power level of the first channel during a first measurement interval and a second power level of the second channel during a second measurement interval. The processor is coupled to the measuring unit and to the switch. The processor adjusts the first power level and the second power level to minimize a difference between a measured value of a control parameter and a target value of the control parameter. The drive unit is controlled by the processor. The drive unit delivers the adjusted first and second power levels to the surgical site via respectively the first channel and the second channel during a heating interval.

In an alternate embodiment of the invention a method for controlling power delivery in an electro-surgical instrument is disclosed. The electro-surgical instrument includes a first channel and a second channel for delivery of energy to a surgical site. The method for controlling power comprises the acts of:

determining a target value for a control parameter for the first channel and the second channel;

measuring a first power level of the first channel during a first measurement interval in which the first channel is electrically isolated from the second channel;

measuring a second power level of the second channel during a second measurement interval in which the second channel is electrically isolated from the first channel; and adjusting the first power level and the second power level to minimize a difference between a measured value of the control parameter and the target value of the control parameter, to deliver the energy to the surgical site during an heating interval.

BRIEF DESCRIPTION OF THE FIGURES

The above and other objects and advantages of the invention will be apparent upon consideration of the following detailed description, taken in conjunction with the accompanying drawings, in which like reference numerals refer to like parts throughout.

DETAILED DESCRIPTION

Accurate determination of the tissue electrical impedance is important in RF electro-surgery since it is a guiding parameter for the surgeon and relates directly to the intended medical benefit. This invention is an improved method and apparatus for tissue electrical impedance determination and electrical power control for such surgeries. The tissue electrical impedance determination and associated power control is improved relative to the prior art methods in that the uncertainties in determining the actual tissue impedance are reduced in two ways. First, this invention makes the impedance determining measurements less prone to noise-related uncertainties. Second, this invention eliminates measurement uncertainties due to electrical cross-talk between multiple electrode channels.

Figure 1:
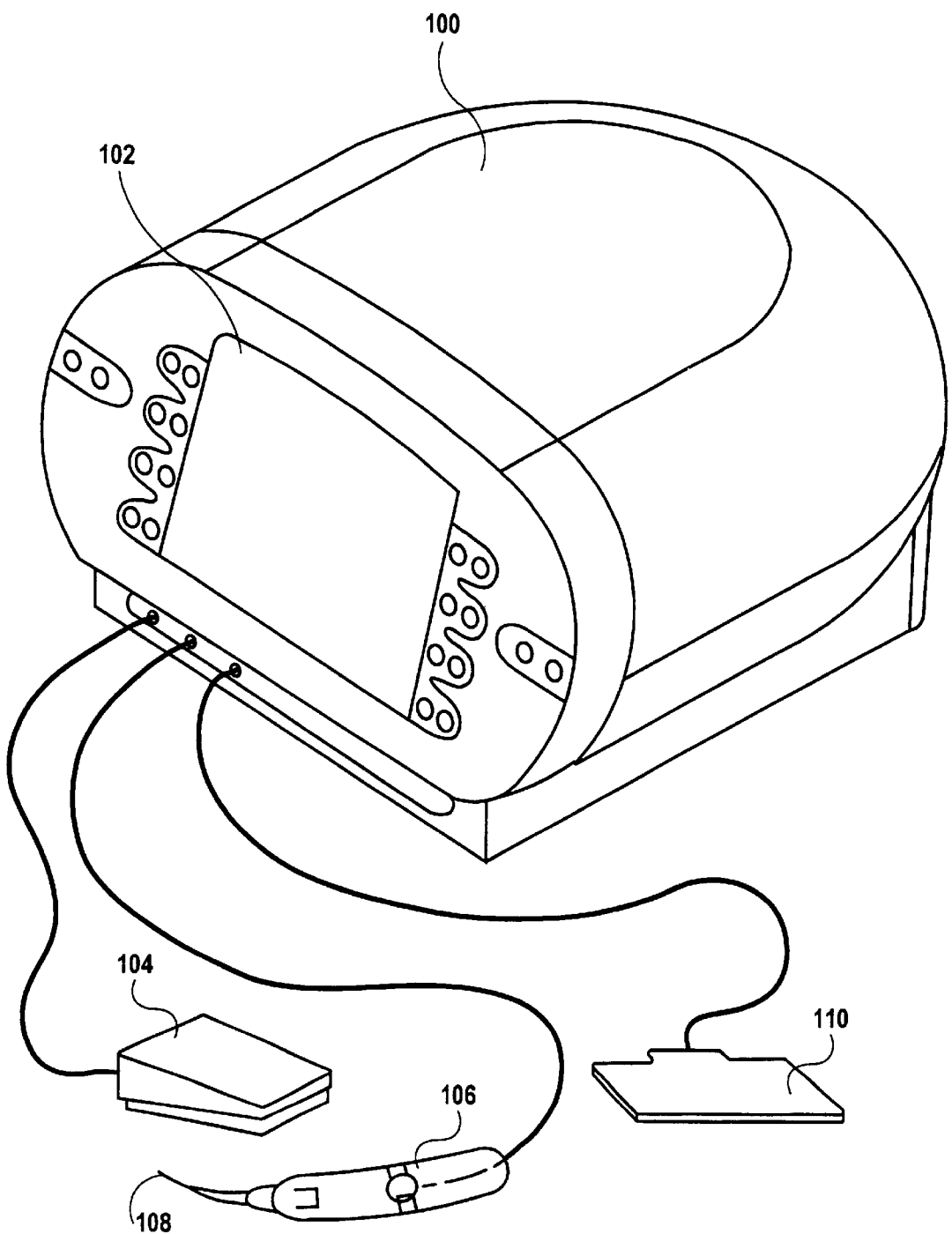
FIG. 1 shows the apparatus for a typical embodiment of the RF electro-surgical device.

FIG. 1 shows the apparatus for a typical embodiment of the RF electro-surgical device. The system comprises an RF power supply 100 with a user input and display panel 102, a foot switch 104, a surgical handset 106 with a surgical probe 108 and an electrical grounding pad 110.

The RF power supply 100 converts the low frequency electrical energy supplied by a wall connection (not shown)

into the high frequency or RF energy necessary for surgery. The user input and display panel 102 displays relevant parameters and provides buttons and switches for user input to the control systems. The foot switch 104 connected to the power supply provides means for switching the unit on and off. The surgical handset 106 is also connected to the power supply and is the means for delivering the RF energy to the surgical probe 108. The probe has one or more probe electrodes. The electrical grounding pad 110 is also connected to the power supply and floats at a reference electric potential. Other embodiments of this invention have no electrical grounding pad.

Figure 2:
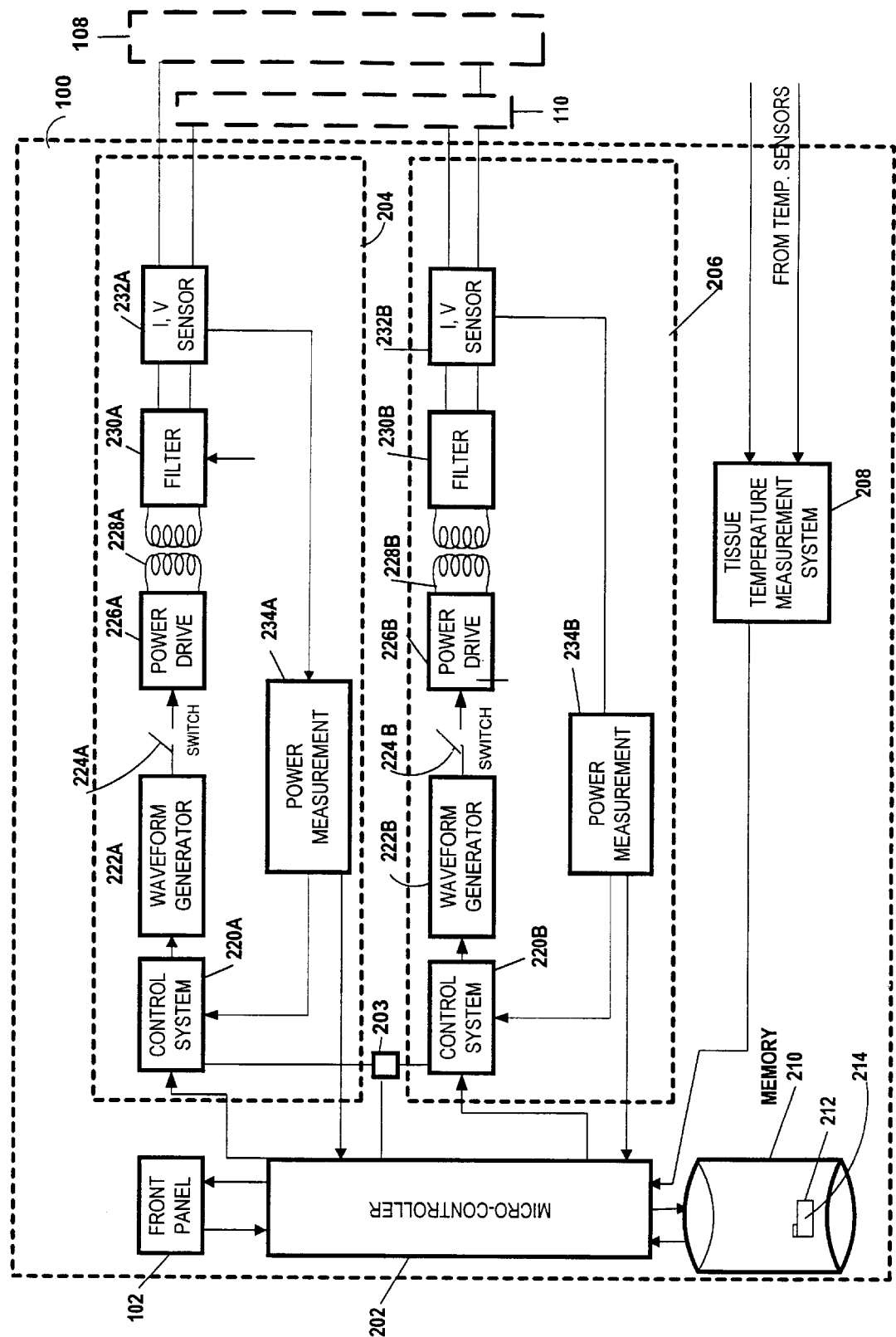
FIG. 2 shows a block diagram showing elements of the system hardware architecture.

FIG. 2 shows a block diagram showing elements of the system hardware architecture of an exemplary embodiment. FIG. 2 shows a block diagram of the RF power supply 100, surgical probe 108 and grounding pad 110. Within the power supply, the user input and display panel 102, microcontroller, a.k.a. processor 202, first and second electrode channels 204 and 206, temperature measurement system 208, memory unit 210, memory files 212, control parameter schedule 214, and RF oscillator 203 are indicated. Electrode channels 204 and 206 are identical, each comprising a control system 220A–B, waveform generator 222A–B, an isolation switch 224A–B, a power drive 226A–B, a transformer 228A–B, a filter 230A–B, current and voltage sensors 232A–B, and power measurement system 234A–B.

In FIG. 2, the user input and display panel 102 is connected to the microcontroller 202 which is connected to the memory unit 210 including memory files 212, including a control parameter schedule 214. The control parameter schedule, a.k.a. profile contains data correlating target control parameters, e.g. temperature and power as a function of time. Exemplary control parameters are power and tissue temperature at the surgical site. Other control parameters are apparent to persons skilled in the art. The micro-controller is connected with the identical electrode channels 204 and 206 and also to the tissue temperature measurement system 208 and the RF oscillator 203. Within each electrode channel, the control systems 220A–B are connected to the microcontroller as well as to the RF oscillator and the tissue temperature measurement system. The control system also connects to the waveform generators 222A–B. The waveform generators are connected to the power drive 226A–B through the isolation switches 224A–B. The RF signals from the transformer 228A–B feed into filters 230A–B. The current and voltage sensors 232A–B connect to the filter, grounding pad 110, surgical probe 108 and the power measurement systems 234A–B.

The micro-controller 202 implements control programs and logic contained in memory files 212, providing the principal intelligence of the control system including the selection of values for time scales and power levels. To act as a means for control, the microcontroller is in two way communication with the user through user input and display panel 102 as well as receives input from the RF oscillator 203, and power and tissue temperature measurement systems 234A–B, 208A–B. The microcontroller is also coupled to memory 210 from which it can obtain the control parameter schedule 214. Control variables are passed to control systems 220A–B to achieve the desired amplitude, frequency, and phase of the electrode potentials.

The RF oscillator and waveform generator 222A–B generate RF oscillations that modulate the output of the power drive 226A–B. Power is coupled through transformer 228A–B by the principle of induction, isolating the patient from direct current (DC). Further frequency filtering is accomplished by filter 230A–B. Collectively components 220A–B through 226A–B constitute drive units for which there are numerous alternate embodiments known to those skilled in the art. Numerous substitutions are possible for the above described components without departing from the teachings of this invention. Current and voltage sensors 232A–B provide required signals for the power measurement systems 234A–B to determine the actual power transferred to the tissue by the current passing between the surgical probe 108 to grounding pad 110.

Figure 3:
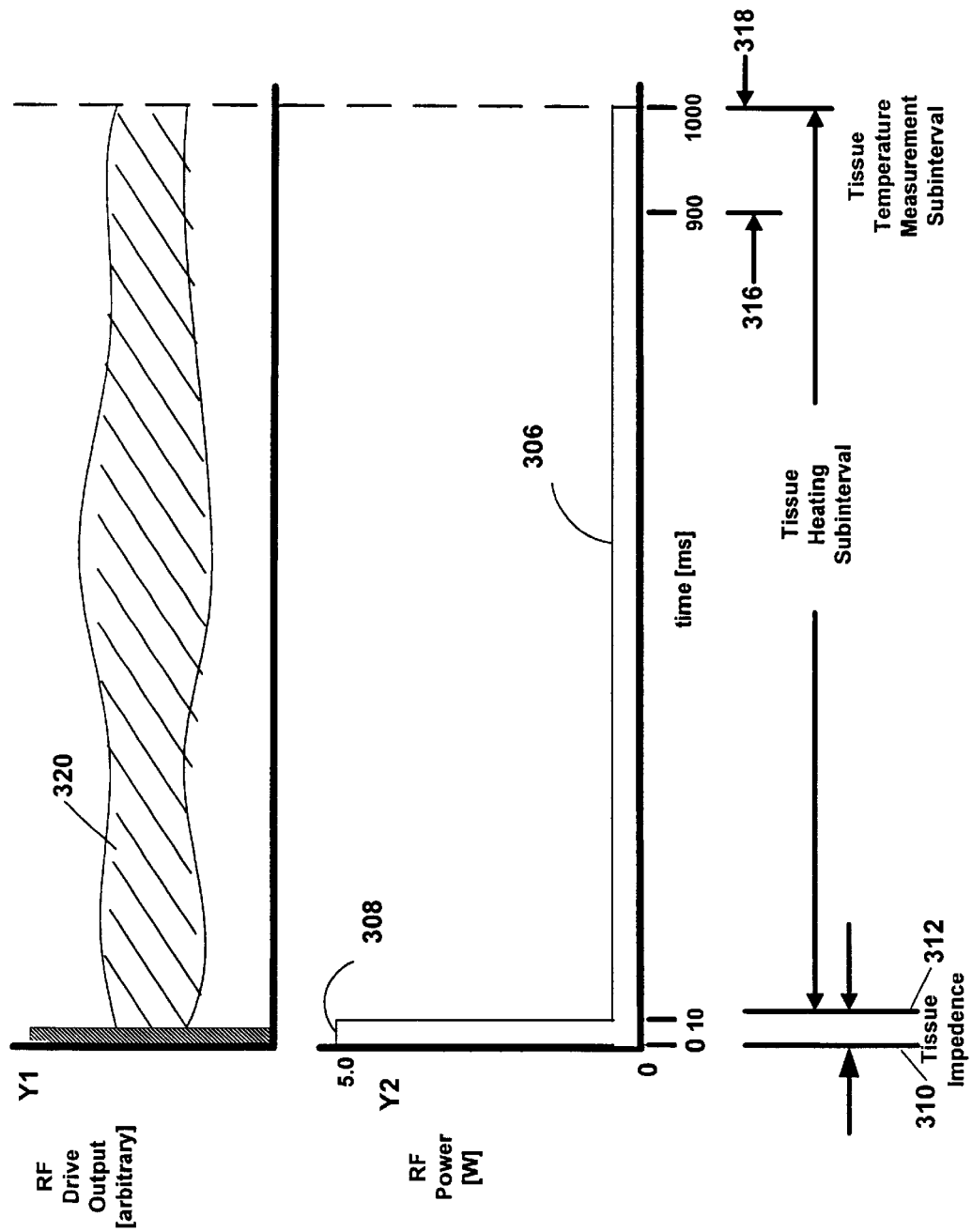
FIG. 3A shows a graph of power versus time for a single electrode probe illustrating the time sub-intervals for impedance determination, tissue heating and tissue temperature measurement time.
FIG. 3B shows a graph of RF power supply output versus time for a single electrode probe illustrating the time sub-intervals for impedance determination, tissue heating and tissue temperature measurement time.

FIG. 3A and FIG. 3B show graphs of power versus time and RF power supply drive parameter versus time for a single electrode probe. FIGS. 3A–B illustrate the time interval multiplexing of an overall system timing cycle, showing the impedance determination, tissue heating and tissue temperature measurement time sub-intervals within an overall system timing cycle. The power control system governs the circuit power on significantly smaller time scales.

As shown in FIG. 3A and FIG. 3B, the overall system timing cycle is typically one second in duration. Over this timing cycle, time markers 310, 312, 316, and 318 bound several time sub-intervals. The sub-interval bounded by time markers 310 and 312 is devoted to determining the electrical impedance of the tissue. This sub-interval is typically 10 milliseconds in duration. Another sub-interval, bounded by time markers 312 and 318, is devoted to the application of RF energy to heat the tissue. This tissue heating sub-interval is typically 900–1000 milliseconds in duration. It is obvious to those skilled in the art that the total time sub-interval for determination of the tissue impedance may be further subdivided into a number of time sub-intervals for sequentially determining the tissue impedance at each of several electrode locations in a multi-channel embodiment.

During each tissue impedance measurement interval, all of the electrodes except the selected electrode are electrically isolated from the system by isolation switches 224. When isolated, no current flows through the electrode channel. Once all electrodes except that of interest are isolated, a comparatively high RF power 308 (typically 5 Watts) is applied to the single electrode and a tissue impedance determination is made from the current and voltage measurements made with the current and voltage sensors 232. The micro-controller repeats the measurements on each electrode channel in succession until the impedances of the tissue along the current paths from each electrode have been determined.

As described, a comparatively high RF power is applied through the probe electrode on each channel during the time sub-interval for tissue impedance determination. Typically, the power control system holds this first power level constant during the sub-interval by comparing a measured power to a target power level. While powerful currents pass through the tissue, the period of time during which high power is applied is sufficiently brief that no significant tissue heating or other undesirable effects occur. The application of a comparatively high current is necessary during this time interval to ensure a signal to noise ratio that is compatible with an accurate impedance determination. This feature, along with the mitigation of inter-electrode coupling during the measurement time, are major advantages of this invention over prior art methods.

The tissue heating time interval is bounded by time markers 312, 318. Typically, it is 900–1000 ms in duration. During this interval, a much smaller second power level is applied to the tissue 306, typically 0.5 Watt. Control is applied to the circuit to maintain a desired power for each electrode channel throughout. Typically, the power is held constant over this time sub-interval. Although the power for each electrode channel is typically held constant, the system allows for different power levels amongst the electrode channels.

FIG. 3A shows, as an example, the maintenance of a constant power level during the period of tissue heating. The envelope of the RF output necessary to deliver the constant power 320 is in FIG. 3B. The drive parameter envelope varies during the tissue heating period due to changes in the tissue impedance caused by Joule heating.

FIG. 3A and FIG. 3B also show the time subinterval for tissue temperature measurement. This subinterval is bounded by time markers 316, 318 and occurs near the end of the tissue heating sub-interval. As described, the tissue temperature measurements are made immediately prior to tissue impedance determination in the subsequent system timing cycle. This reduces the time interval between the tissue temperature measurement and the application of the power level based on that temperature.

Figure 4:
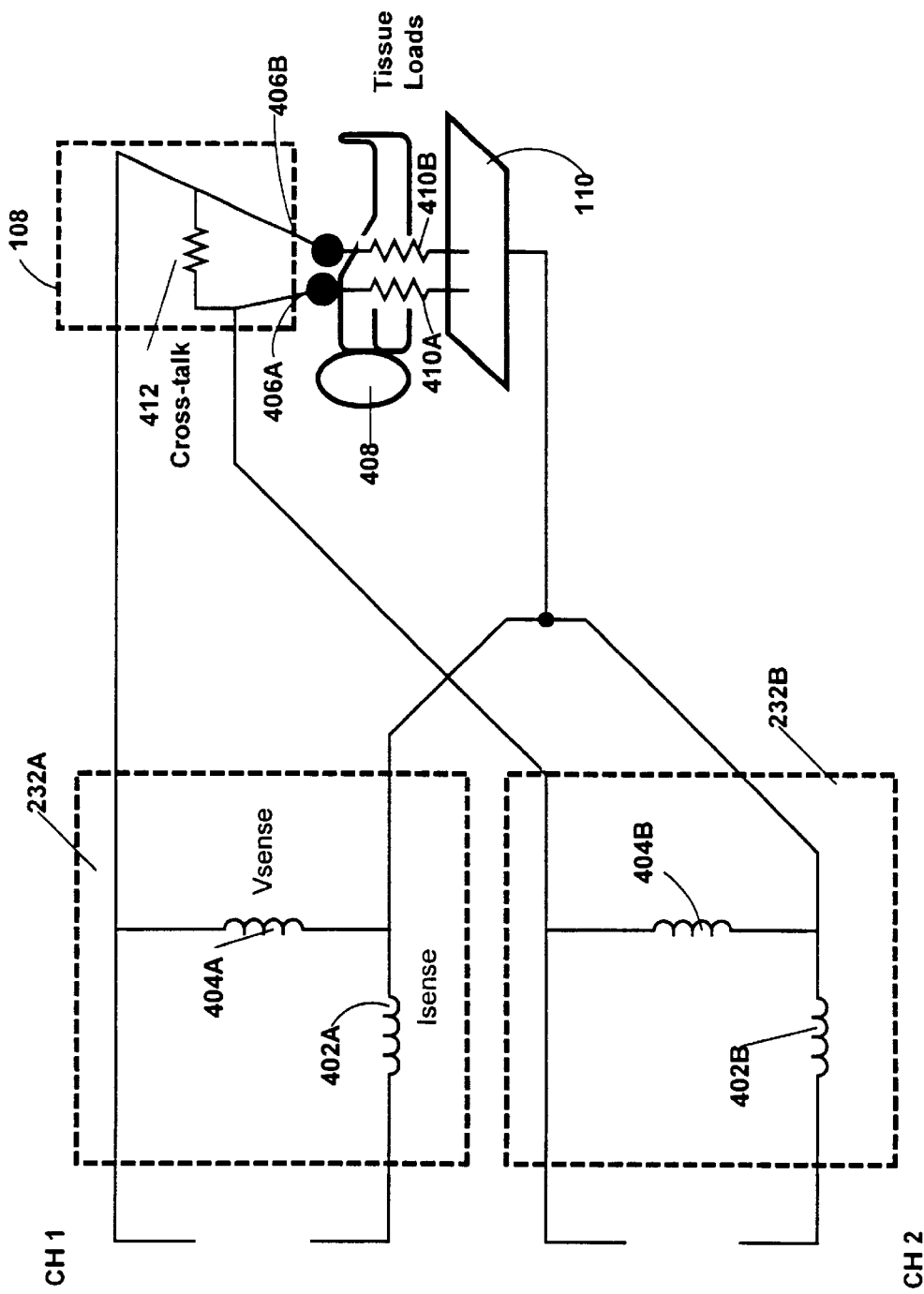
FIG. 4 shows a schematic illustrating electrical hardware elements of the surgical apparatus in a multi-channel embodiment.

FIG. 4 shows a system with two probe electrodes. This two channel system includes current and voltage sensors 232A–B for each channel, surgical probe 108 electrodes 406A–B and electrical grounding pad 110. Within each current and voltage sensor 232A–B, there is a current sensor 402A–B and voltage sensor 404A–B. Within the surgical probe 108, there is an electrode 406A and 406B for each channel. The electrodes are in contact with tissue 408 and the tissue is in contact with the electrical grounding pad. The equivalent electrical circuit representing the tissue impedance from the electrodes to the grounding pad 410A–B and the inter-electrode coupling (cross-talk) impedance 412 is also shown.

In FIG. 4, each of the current and voltage sensors 232A–B are connected to their respective electrodes 406A–B in the surgical probe 108 as well as to the common electrical grounding pad 110. The tissue is connected to the electrodes and the grounding pad. The grounding pad is connected to the tissue and the current and voltage sensors 232A–B.

When each electrode 406A–B is connected to the RF generator (not shown), a RF electrical current flows through the tissue to the grounding pad 110. As this occurs, current and voltage sensors 402A–B, 404A–B act as a means to determine the RF power applied to the tissue, as well as the electrical impedance of the tissue between the electrode tip and the grounding pad. The relationships between current, voltage, power and impedance are well known to persons skilled in the art. Note that with all of the electrodes except the one of interest isolated by switches 224A–B (see FIG. 2) there is no significant coupling between the electrodes in the surgical probe causing current flow between them. This is beneficial for an accurate tissue impedance determination. It is obvious to those skilled in the art that the isolating switch may be located elsewhere than shown in FIG. 2.

Figure 5:
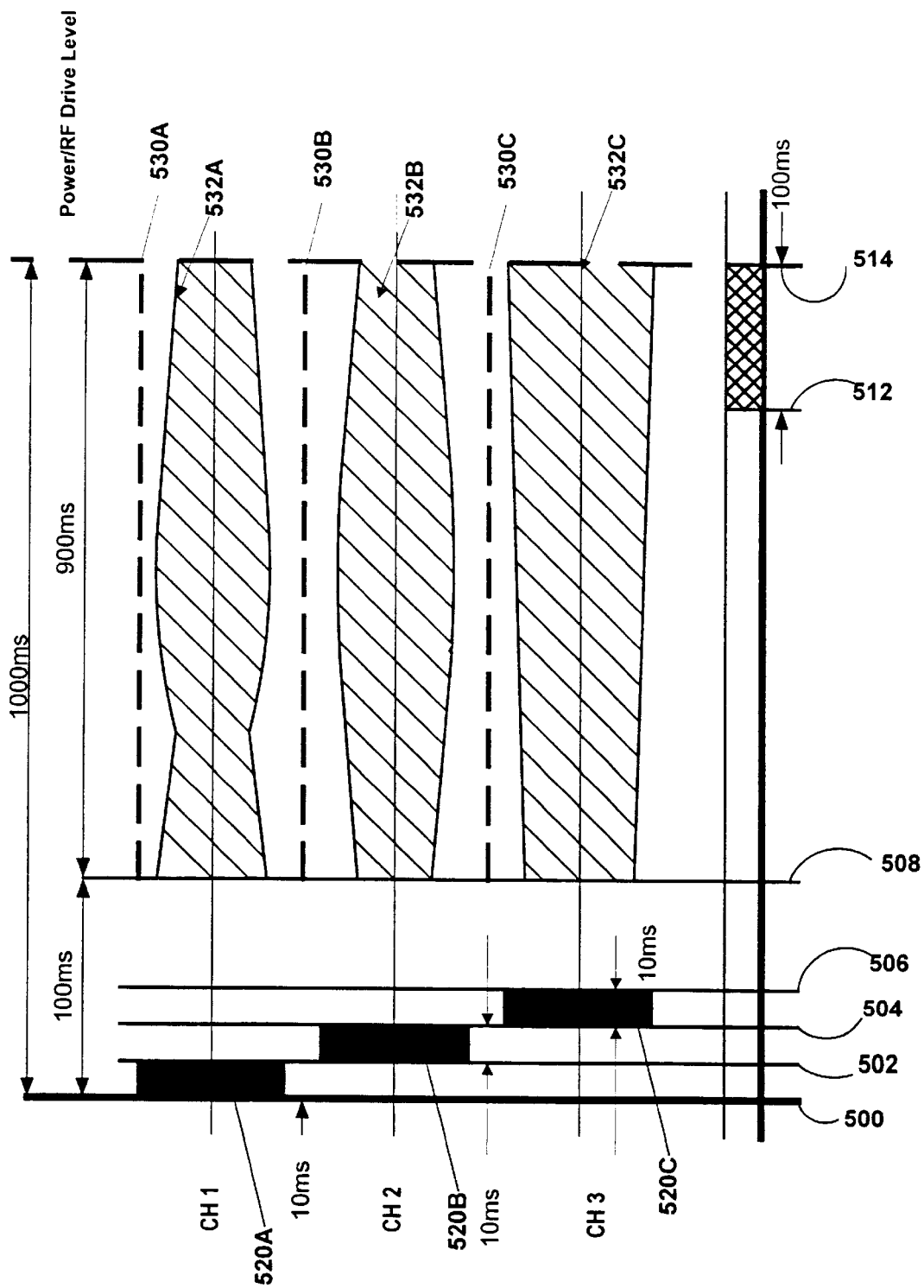
FIG. 5 shows a graph of power versus time and RF power supply output versus time for a multiple electrode probe illustrating the impedance determination, tissue heating and tissue temperature measurement time subintervals.

FIG. 5 shows a graph of power versus time and RF power supply output versus time for a multiple electrode probe. FIG. 5 illustrates the impedance determination, tissue heating and tissue temperature measurement time sub-intervals within an overall system timing cycle and is similar to the case of a single channel described in FIG. 3. As in the case of a single channel, the power control systems govern the circuit power on significantly smaller time scales.

As in the case of the single channel, each of the multiple channels has several sub-intervals within the overall system timing cycle of approximately one second duration. The sub-intervals are defined by time markers 500, 502, 504, 506, 508, 512, 514. For each channel, there is an tissue heating time sub-interval bounded by time markers 508 and 514. However, as seen in FIG. 5, the tissue heating time sub-intervals for all channels coincide. Each channel also has an impedance determination sub-interval 520A–C that follow each other in sequence. The total impedance determination sub-interval for all channels is bounded by time markers 500 and 508 and is typically 100 milliseconds in duration. In this interval time division multiplexing allows each electrode to be electrically isolated from all others while its impedance is measured. The impedance measurement is carried out at a high power level. The high power level allows an accurate determination of impedance. Such a determination would be more difficult at the relatively low power levels used during the tissue heating time subinterval. Also shown in FIG. 5 is a tissue temperature measurement time sub-interval bounded by time markers 512, 514 near the end of the overall timing cycle. The tissue temperature sub-interval is approximately 100 milliseconds in duration. During all of the above time sub-intervals, the power control systems operate on significantly shorter time scales to maintain the desired power 530A–C on each channel by varying the RF drive parameters 532A–C.

As was the case for a single channel, significantly different power levels are applied to the tissue for the impedance determination and tissue heating. In order to have the signal to noise ratio necessary for an accurate impedance determination a comparatively high power is applied to each electrode channel during that time interval. However, as previously described, the duration of this high power application is sufficiently short so that no significant tissue heating occurs. During the subsequent tissue heating interval, a much lower RF power is applied to the tissue on all channels. While the power level during this interval is comparatively low, the application persists over a time interval several orders of magnitude longer than that for the tissue impedance determination. During the period of tissue heating, the power circuits of each channel are controlled to maintain a constant power under a varying impedance. A tissue temperature measurement is made near the end of the heating interval.

Figure 6:
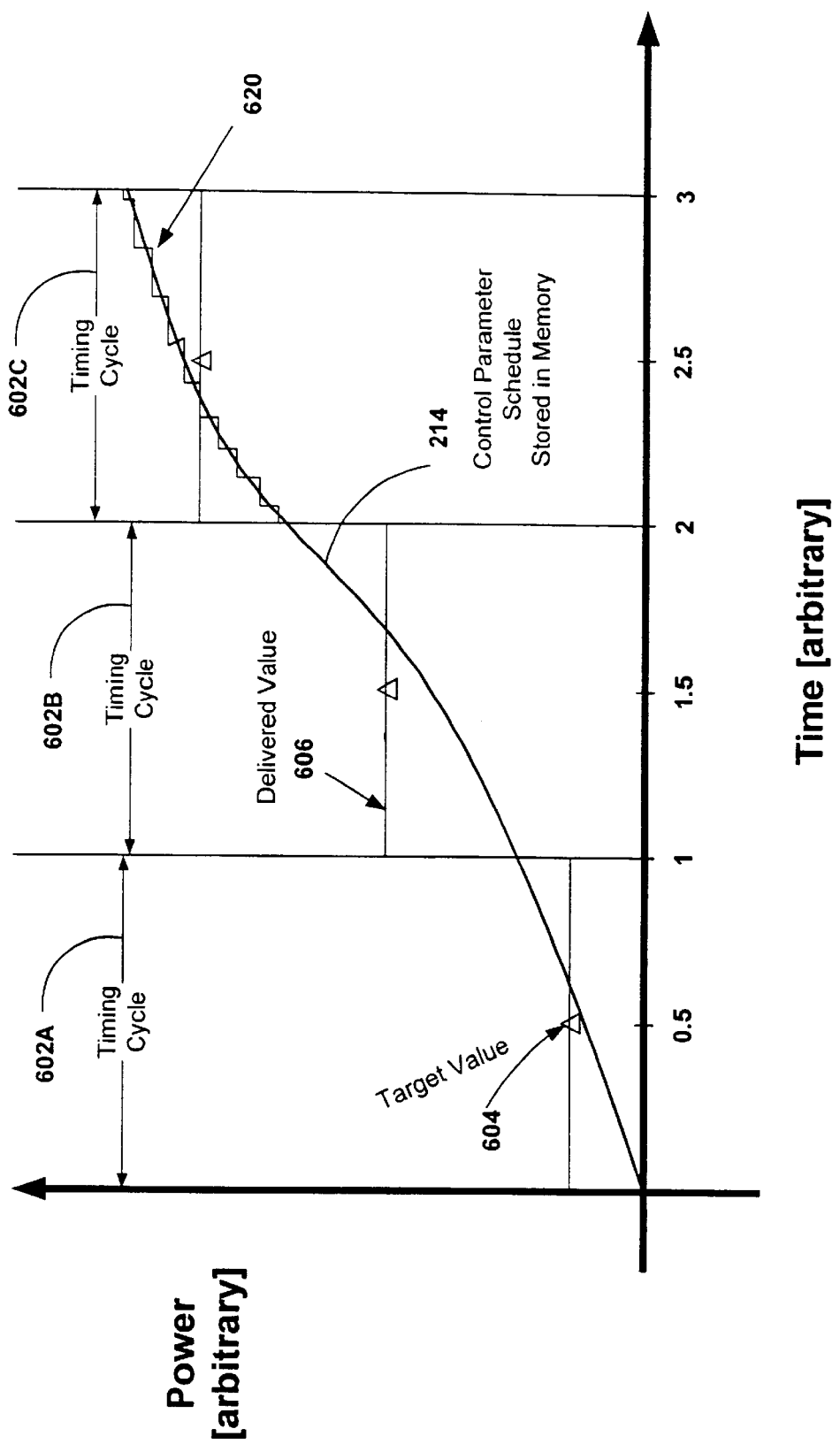
FIG. 6 shows a graph of power versus treatment time illustrating a power time schedule, target power and power delivered by the power control system.

FIG. 6 shows a graph of power versus treatment time illustrating a power time schedule, target power and power delivered by the power control system under a exemplary control law. It illustrates the use of the power control system to accomplish the intended medical function by delivering prescribed power to the tissue site. FIG. 6 shows a control parameter schedule 214, with power as the control parameter. Three overall system timing cycles 602A–C of one second duration each are shown. During each overall system timing cycle, the micro-controller 202 (see FIG. 2) receives inputs from power and temperature measurements and executes control laws based on those and other system parameters. Under an exemplary control law, the micro-controller calculates a target value of power 604 and control is applied to each electrode channel 204A–B (see FIG. 2) to maintain a constant delivered value 606 of power over the timing interval. The target value of the control parameter may be updated as desired to follow the control parameter schedule to a desired accuracy. This is illustrated by the comparative frequency of target value updates in timing cycles 602A–C. It is obvious to those skilled in the art that the system can be configured to follow other appropriate control parameters, such as tissue temperature. It is equally obvious to those skilled in the art that the system can be configured to follow other power control laws.

Figure 7:
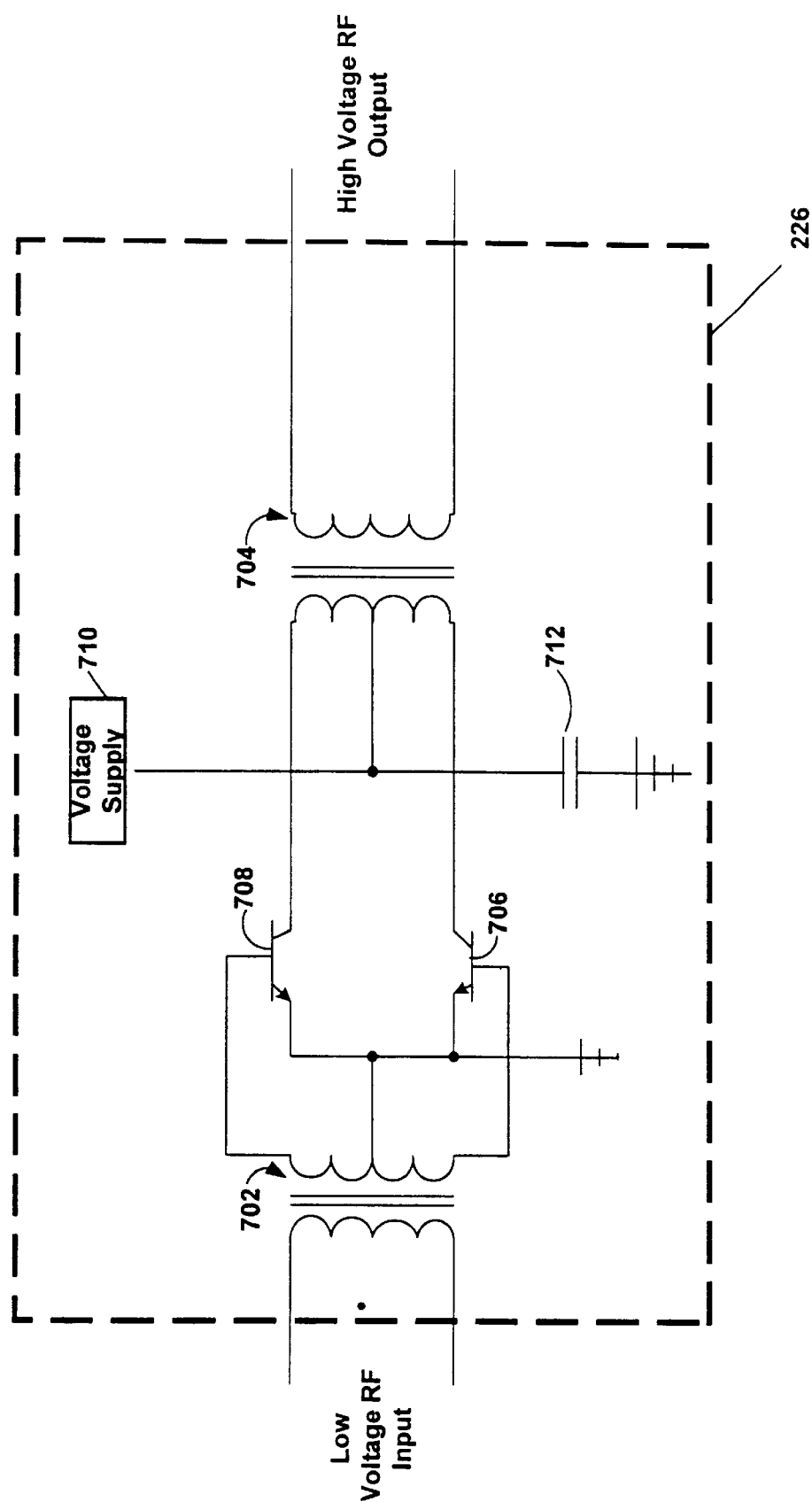
FIG. 7 shows a schematic illustrating the electrical hardware elements of a power drive element.

FIG. 7 shows a schematic illustrating the electrical hardware elements of a power drive element 226. The power drive contains two transformers 702 and 704, two transistors 706 and 708, positive voltage supply 710 and an decoupling capacitor 712.

In FIG. 7, transformer 702 is connected to the RF oscillator on one side and the transistors 706 and 708 on its other side. The center tap of the transformer is also connected to the transistors 706 and 708. The winding of the second transformer 704 are connected to the positive voltage supply 710 and decoupling capacitor 712 on one side and on the other side they form the output of the device.

The transformer 702 serves to isolate the unit from the RF waveform generator 222 (see FIG. 2) that provides its input. Through the principal of electrical induction, radio frequency oscillations are induced in the RF power supply from the RF waveform generator. The positive voltage supply 710 in conjunction with the second transformer 704 act to modulate the amplitude of the RF voltage in the circuit. Through the principal of electrical induction the RF signals are transferred to the output across the transformer 704.

Figure 8:
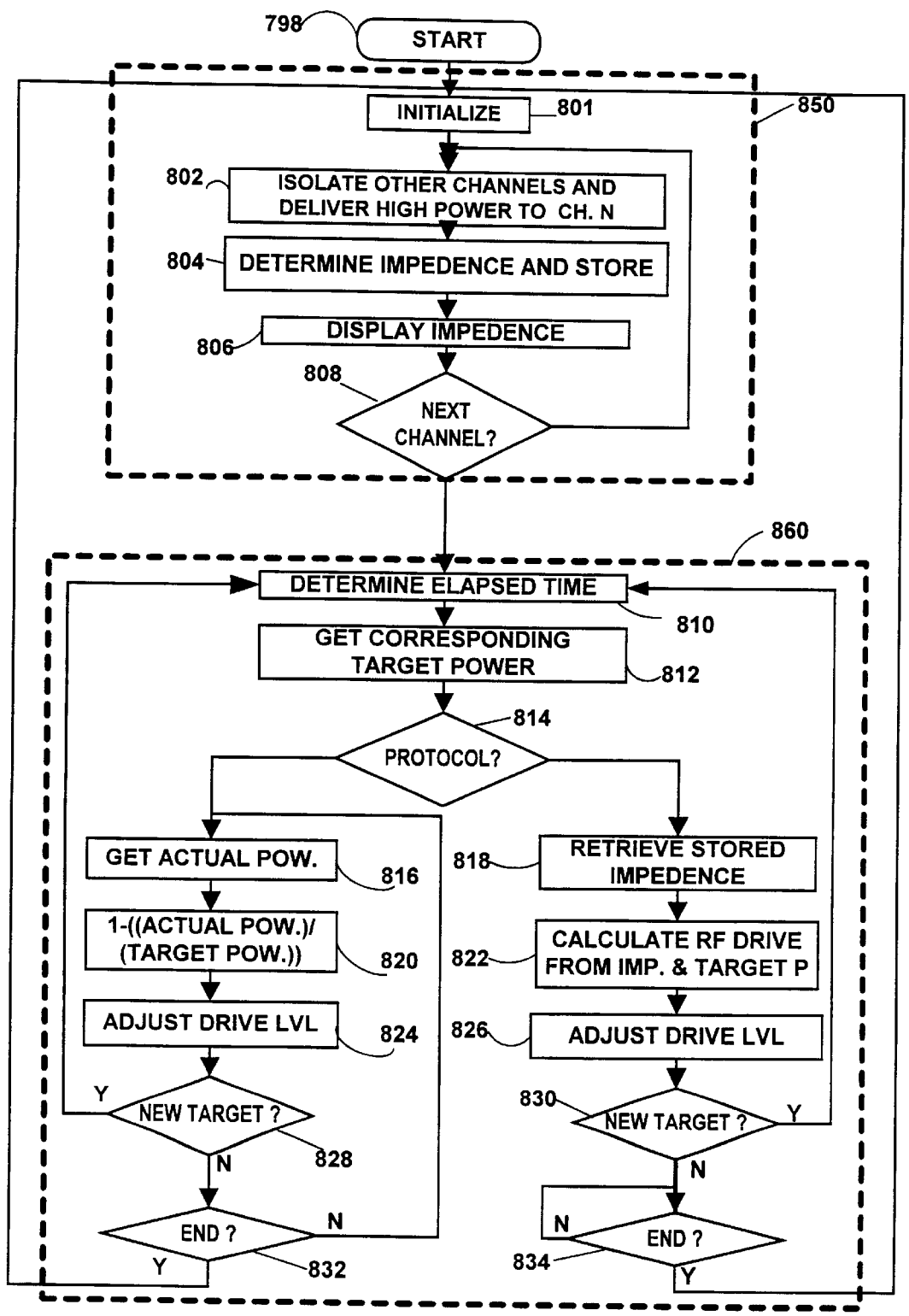
FIG. 8 shows a process flow chart illustrating the method for tissue impedance determination and power control.

FIG. 8 shows a process flow chart for this method of tissue electrical impedance determination and electrical power control. The process shown in FIG. 8 is implemented by micro-controller 202 (see FIG. 2). In alternate embodiments, the process implementation is divided between the micro-controller and analog hardware in control system 220A–B (see FIG. 2). The process begins by startup and initialization of the device in process block 798. During startup, the system initializes itself, performs several self-tests and uploads information from the memory and receives information input by the user from the front panel. Clocks and other variables requiring initialization are set in block 801.

Within the overall system timing cycle illustrated, control first passes to sequence 850 where the tissue impedance determinations are accomplished. In 802, the micro-controller 202 electrically isolates all but the first channel and then applies a comparatively high RF power only to that channel. Control then passes to process block 804 where the electrical impedance in the tissue is determined from measurements of current and voltage in the energized channel. The resulting the value is stored. Control then passes to process block 806 where the value of the tissue impedance is displayed to the user at the user input and display panel 102 (see FIG. 1). Control then passes to decision block 808 where the system can repeat the preceding process for subsequent electrode channels or proceed once the tissue impedance across all of the electrodes is determined.

Once the tissue impedance has been measured at each electrode channel, control passes to sequence 860 were the tissue heating is accomplished. Sequence 860 begins with block 810 where the micro-controller 202 (see FIG. 2) determines the elapsed time from the start of the treatment. This corresponds to the abscissa shown in FIG. 6. Following this, control passes to process block 812 where the micro-controller calculates a target value of the control parameter. In this exemplary embodiment, power is the control parameter. Thus, the micro-controller calculates a target power from the control parameter schedule 214 (see FIG. 2). Control then passes to decision block 814.

At decision block 814, the system chooses a power control protocol. In one embodiment, with power as the control parameter, there are two power control protocols to choose from. Under the first power control protocol, the power delivered to the tissue site from an electrode is calculated from the measurements of current and voltage in process block 816. Control then passes to process block 820, where the fractional difference between the actual power delivered and the target power, or fractional error, is calculated. Control then passes to process block 824 where a RF drive parameter is adjusted, altering the RF power to minimize the fractional error and maintain the constant target power delivered through the electrode. This value is communicated to the power control system 220 (see FIG. 2). Control then passes to decision block 828 where an evaluation is made as to whether an update of the targeted value of power is desired. If a new target value for the power is not desired, control passes to decision block 832. At decision block 832, an evaluation is made as to whether the tissue heating time limit is over. If it is, then the system returns to 850 and another overall system timing cycle begins with tissue impedance measurements on each electrode channel.

An alternate power control protocol proceeds from decision block 814 by retrieving the stored tissue impedance at process block 818. Control then passes to process block 822 where the RF drive parameter required to deliver the target value of power is calculated directly, assuming the stored tissue impedance value from the previous impedance determination interval. Control then passes to process block 826 where the RF drive parameter is adjusted to achieve the target value. This value is communicated to the power control system 220 (see FIG. 2). Control then passes to decision block 830 where an evaluation is made as to whether an update of the targeted value of power is desired. If a new target value for the power is not desired, control passes to decision block 834. At decision block 834, an evaluation is made as to whether the tissue heating time period is over. If it is, then the system returns to 850 and another overall system timing cycle begins with tissue impedance measurements on each electrode channel.

In an alternate embodiment of the invention temperature rather than power constitutes the control parameter in the control parameter schedule 214. In that embodiment the protocol followed compares current, previous temperature, and target temperature and impedances of each electrode and determines the amount of error in the desired versus actual temperature of the surgical site. Using this determination power is adjusted accordingly and the appropriate "heating" voltages for maintaining the target temperature at the surgical site are imposed by the waveform generator 222A–B and the power drive 226A–B.

While this invention has been particularly shown and described with reference to a preferred embodiment thereof, it will be understood by those skilled in the art that various changes in form and detail may be made therein without departing from the spirit and scope of the invention.

What is claimed is:

1. A method for controlling power delivery in an electrosurgical instrument including a first channel and a second channel for delivery of an energy to a surgical site, and the method for controlling power comprising the acts of:

determining a target value for a control parameter for the first channel and the second channel, the target value determined by matching an elapsed operating time with a corresponding control parameter profile of a control parameter schedule listing values for the control parameter as a function of time;

measuring a first power level of the first channel during a first measurement interval in which the first channel is electrically isolated from the second channel;

measuring a second power level of the second channel during a second measurement interval in which the second channel is electrically isolated from the first channel; and adjusting the first power level and the second power level to minimize a difference between a measured value of the control parameter and the target value of the control parameter, to deliver the energy to the surgical site during a heating interval.

2. The method of claim 1, wherein the measured value and the target values of the control parameter in said determining and adjusting acts correspond to a one respectively of:

an actual temperature at the surgical site together with a desired temperature of the surgical site; and an actual power delivered to the surgical site together with a desired power delivered to the surgical site.

3. The method of claim 1, wherein the act of measuring the first power level further comprises the act of:

terminating delivery of energy to the second channel to electrically isolate the first channel.

4. The method of claim 3, wherein the act of measuring the second power level further comprises the act of:

terminating delivery of energy to the first channel to electrically isolate the second channel.

5. The method of claim 1, wherein the acts of measuring the first power level and the second power level further comprises the acts of:

a) applying a fixed voltage to the first channel and the second channel; and b) measuring a corresponding impedance for each of the first channel and the second channel;

and wherein the act of adjusting the first power level and the second power level further comprises the act of:

calculating voltages to be applied to the first channel and the second channel on the basis of the corresponding impedances of the first channel and the second channel.

6. The method of claim 5, wherein said act of measuring a corresponding impedance further comprises the act of:

measuring a current and a voltage delivered on each of the first and the second channel.

7. The method of claim 5, wherein the fixed voltage applied during said applying act exceeds the heating voltages applied during said act of adjusting the first power level and the second power level.

8. The method of claim 1, wherein the acts of measuring the first power level and the second power level further includes the act of:

time interval multiplexing an application of a fixed voltage to the first channel and the second channel.

9. The method of claim 8, wherein the fixed voltage applied during said act of time division multiplexing exceeds voltages applied to said first channel and said second channel during said adjusting act.

10. The method of claim 1, wherein the first interval and the second interval are together less in duration than the heating interval.

11. The method of claim 10, wherein the first interval and the second interval are chosen to minimize the effect of energy delivered to the surgical site during said intervals.

12. The method of claim 1, wherein a total power applied to the surgical site during said first and said second measuring acts is fractionally related to the power applied during the heating interval to minimize an effect on the surgical site of the power delivered to the surgical site during said first and said second measuring acts.

13. An apparatus for controlling power delivery in an electro-surgical instrument including a first channel and a second channel for delivery of energy to a surgical site, and the apparatus for controlling power comprising:

a switch for electrically isolating the second channel during a first measurement interval and electrically isolating the first channel during a second measurement interval; and a power measuring unit coupled to the first and the second channel for measuring a first power level of the first channel during a first measurement interval and a second power level of the second channel during a second measurement interval;

a processor coupled to the measuring unit and to the switch for adjusting the first power level and the second power level to minimize a difference between a measured value of a control parameter and a target value of the control parameter;

a storage unit with a control parameter profile listing values for the control parameter as a function of time wherein the processor couples to the storage unit to obtain the target value by matching an elapsed operating time with the corresponding control parameter profile; and a power drive unit controlled by the processor to deliver the adjusted first and second power levels to the surgical site via respectively the first channel and the second channel during a heating interval.

14. The apparatus of claim 13, wherein the measured value and the target values of the control parameter correspond to a one of respectively:

an actual temperature at the surgical site together with a desired temperature of the surgical site; and an actual power delivered to the surgical site together with a desired power delivered to the surgical site.

15. The apparatus of claim 13, wherein the switch decouples the drive unit from the second channel during the first measurement interval and decouples the drive unit from the first channel during the second measurement interval.

16. The apparatus of claim 13, further comprising:

a first sensor and a second sensor for measuring respectively a voltage together with a current on the first channel and the voltage together with a current on the second channel, and each of the sensors coupled to the measuring unit.

17. A method for controlling power delivery in an electro-surgical instrument including a plurality of channels for delivery of an energy to a surgical site, and the method for controlling power comprising the acts of:

measuring in a first time interval, the impedance of each of said channels measured by sequentially isolating each channel from others of the channels; and adjusting in a second time interval, power levels of said channels to minimize a difference between a measured value of a control parameter and a target value of the control parameter, the target value determined by matching an elapsed operating time with a corresponding control parameter profile of a control parameter schedule listing values for the control parameter as a function of time, to deliver the energy to the surgical site during a heating interval.

* * * * *